(12) United States Patent
Thakur et al.

(10) Patent No.: US 11,774,450 B2
(45) Date of Patent: Oct. 3, 2023

(54) APPARATUS FOR DETECTION OF PROTEOLYTIC ACTIVITY IN A BIOLOGICAL SAMPLE

(71) Applicants: Shubhendra Singh Thakur, Nagpur (IN); Deovrat Begde, Nagpur (IN); CURO Biosciences Pvt. Ltd., Nagpur (IN)

(72) Inventors: Shubhendra Singh Thakur, Nagpur (IN); Deovrat Begde, Nagpur (IN)

(73) Assignees: Shubhendra Singh Thakur, Nagpur (IN); Deovrat Begde, Nagpur (IN); CURO Biosciences Pvt. Ltd., Nagpur (IN)

( * ) Notice: Subject to any disclaimer, the term of this patent is extended or adjusted under 35 U.S.C. 154(b) by 169 days.

(21) Appl. No.: 17/153,896

(22) Filed: Jan. 21, 2021

(65) Prior Publication Data
US 2021/0223245 A1 Jul. 22, 2021

(30) Foreign Application Priority Data
Jan. 21, 2020 (IN) .............................. 202021002695

(51) Int. Cl.
*G01N 33/573* (2006.01)
*G01N 33/574* (2006.01)
*G01N 33/58* (2006.01)

(52) U.S. Cl.
CPC ......... *G01N 33/573* (2013.01); *G01N 33/574* (2013.01); *G01N 33/582* (2013.01); *C12Y 304/17* (2013.01)

(58) Field of Classification Search
CPC .. G01N 33/573; G01N 33/574; G01N 33/582; G01N 33/526; C12Y 304/17; C12Y 304/24; C12Q 1/37
See application file for complete search history.

(56) References Cited

U.S. PATENT DOCUMENTS 6,037,138 A    3/2000 Moses et al.

FOREIGN PATENT DOCUMENTS

| CA | 2284099 C | 4/2010 | |
| DE | 102014017263 A1 * | 5/2015 | ............... C12Q 1/37 |

(Continued)

OTHER PUBLICATIONS

Thermo Scientific; https://www.thermofisher.com/order/catalog/product/20278; accessed Oct. 18, 2022 (Year: 2016).*

(Continued)

*Primary Examiner* — Lora E Barnhart Driscoll
*Assistant Examiner* — Candice Lee Swift (57) ABSTRACT

The present disclosure illustrates an apparatus (100) and method (400) for detection of proteolytic activity of an enzyme and for assessing the level of matrix metalloproteinases in a biological sample. The apparatus (100) comprises a tubular outer jacket (109) with a seal cap (107). The apparatus (100) comprises one or more inner segment tubes (101, 103, 105) connected to each other at a lower end opening of each of the one or more tubes. The one or more inner segment tubes (101, 103, 105) comprises at least two chambers separated by a protein substrate layer (102, 104, 106). The level of the matrix metalloproteinases is assessed on the basis of number of protein layers digested and the proteolytic activity level of by the biological sample.

14 Claims, 5 Drawing Sheets

(56) References Cited

FOREIGN PATENT DOCUMENTS

| | | | |
|---|---|---|---|
| DE | 102014017263 A1 | 5/2015 | |
| EP | 1295948 B1 | 8/2008 | |
| JP | 4366087 B2 | 11/2009 | |
| KR | 20100105254 A | 9/2010 | |
| KR | 20160110701 A * | 9/2016 | ............. A61K 49/00 |
| WO | 1994005806 A1 | 3/1994 | |

OTHER PUBLICATIONS

"Modified Qiagen gel extraction with MinElute spin column." https://www.protocols.io/view/modified-qiagen-gel-extraction-with-minelute-spin-3byl43yogo5d/v1; accessed Oct. 17, 2022 (Year: 2017).*

* cited by examiner

APPARATUS FOR DETECTION OF PROTEOLYTIC ACTIVITY IN A BIOLOGICAL SAMPLE

CROSS-REFERENCE TO RELATED APPLICATIONS AND PRIORITY

The present application claims priority from Indian Patent Application no. 202021002695 filed on 21 Jan. 2020, the details of which are incorporated herein by a reference.

TECHNICAL FIELD

The present subject matter described herewith, in general relates to an apparatus for detection of enzymes in a biological sample. More particularly, the present subject matter relates to an apparatus for detection of enzymes by determining proteolytic activity level in a biological sample.

BACKGROUND

Nowadays, the number of people living unhealthy lifestyle has increase, as a result of which risk of plausible malignancy and further the need for cancer prognosis is high in such people. Various oral precancerous conditions which may involve Oral submucous fibrosis (OSMF), Leukoplakia, Erythroplakia, Lichen Planus can be detected and cured at initial stage by using different techniques but techniques to predict their likelihood to reach up to a malignant stage perhaps Oral Squamous Cell Carcinoma are still not available. The same is true for detection other disorder conditions like Prognosis of Chronic obstructive pulmonary disease (COPD), Lung Cancer and Diabetes.

Oral cancer is the sixth most common cancer in the world. More than 95% of oral cancers are squamous cell carcinomas (OSCC). In India, the incidence of oral cancer is the highest, accounting for almost one third cases found in the world. Other south Asian countries have also seen jump in Oral malignancies in the recent surveys. Over 5 people in India die every hour because of some type of oral malignancy. The 90% of oral cancer issues have been increased due to smoking and alcohol consumption all over the world.

Conventionally, metastatic malignancy detection from saliva sample or any similar biological sample requires a sophisticated lab setup with high end equipment to perform protocols for Gelatin Zymography, Western Blot, enzyme-linked immunosorbent assay (ELISA) and/or Real-Time quantitative Polymerase chain reaction (qPCR). Such conventional methods known in state of the art are expensive, time taking and are not available abundantly due to its economic burden.

The other malignancy detection methods practiced by person skilled in the art are invasive methods such as biopsy and blood tests. Before going for the expensive tests suggested by Dentists, Oncologists, physiologists and Health practitioners such as Biopsy, ELISA, Real Time Quantitative PCR, MRI and others, it is always beneficial to assess the primary risk of cancer by a non-invasive or non-radiation way.

The major hindrance is that the most of the oral cancer patients undergo diagnosis at the advanced clinical stages, i.e., III and IV stages. Due to the delayed detection, the morbidity rate is potentially high with maximum of 5 years survival rate in 20-25% of the patients. In contrast, early stage oral cancer detections are often highly curable with less morbidity than cancers that are in later stages. These statistics emphasize the importance of early and accurate detection by clinicians.

In addition, early detection of cancer would also lead to fewer side effects from cancer treatments such as chemotherapy and radiotherapy and to a better prognosis. Thus, there is a need for improvement in early detection technique of carcinomas because in the initial stages and in the pre-cancerous stages, when treatment is more effective, and the morbidity is minimal.

The crucial phenomenon linked with the primary malignant tumour is the formation of metastasis. It is complex process formed by the cancerous cells that have left the primary tumour mass and migrate through the blood and lymphatic vessels to seek out new sites throughout the body, described as "tumour cascade". Different tumours have variable tendencies to metastasize. The mechanisms of tumour initiation, progression and invasion are outcome of a complex cross-talk between different cell types within the tumour microenvironment.

In state of the art, Matrix metalloproteinases (hereinafter may be alternatively referred to as 'MMP') are considered to be the key players in the regulation of cell to cell and cell extracellular matrix (hereinafter may be alternatively referred to as 'ECM') interactions. Abnormal activity or expression of MMPs have been known to be involved in tumour progression.

Most popular of all and well characterized are MMP-2 and MMP-9 also known as Gelatinase-A and -B, are extensively studied in cancer progression, perhaps due to ease of their activity profile detection. Gelatin zymography first worked out by C. Heussen and E. B. Dowdle in 1980, is still considered to be the gold standard for characterization of MMP-2 and MMP-9

As compared to MMP-2, MMP-9 has seen to be more related to distant metastasis, lymph node involvement and higher stage of the disease. Particularly, infiltration is the essential and key step of metastasis and important factor in prognosis of oral cancer.

Hence, early detection of metastasis in a biological sample is of great clinical importance. Prognosis and treatment of the malignancy depends upon the tumour stage. The early diagnosis and prediction of metastasis, based on clinical parameters are still difficult, lacking in early diagnostic methods. Presently, cancer prognostic evaluation of any biological sample is based on clinical staging and histological grading which is often not reproducible. Application of MMPs expression and clinical features might be considered as early indicators for the malignancy potential of oral cancer.

Essentially to counter the overexpression of MMPs by the neoplastic cells the body's defence system deploys elicitation of MMP inhibitors like tissue inhibitors of matrix metalloproteinases (TIMPs).

Therefore, there is need to devise a critical tool for the early detection of oral malignant cancer that are sensitive, specific, robust and rapid. There is also a long felt need of an effective and inexpensive device for assessing the risk of malignancy by detecting the level of malignancy or malignant components in biological fluid.

OBJECTIVE OF THE DISCLOSURE

It is an objective of the present disclosure to develop an apparatus enabling a convenient, rapid and cost-effective apparatus for detection of gelatinase activity in biological sample.

It is another objective of the present disclosure to provide a solution for performing a simple non-invasive procedure for detection and plausible cancer or malignancy risk assessment by using a newly casted apparatus.

It is yet another objective of the present disclosure to develop a device for detecting the expression of MMP-2 and MMP-9 in various sample of oral cancer patients, and to evaluate the implications of their expression on clinic pathologic factors, principally on prognosis, using a simple and convenient protein based assay in an innovative kit design.

It is still another objective of the present invention to quantify the active MMP-2 and MMP-9 biomarkers associated with an early prognosis of cancer such as oral cancer from a saliva sample by developing a simple, cost-effective and precise proteolytic activity evaluation kit.

SUMMARY

This summary is provided to introduce concepts related to an apparatus and method for detection of proteolytic activity in a biological sample. This summary is not intended to identify essential features of the claimed subject matter nor it is intended for use in determining or limiting the scope of the claimed subject matter.

In one embodiment, an apparatus for assessment and detection of proteolytic activity level of an enzyme such as metalloproteinases present in a biological sample is illustrated herewith, in accordance with an embodiment of the present disclosure.

The apparatus may comprise a tubular outer jacket with a seal cap. The apparatus may comprise a thin layer of staining dye for staining the biological sample. The tubular outer jacket may house one or more inner segment tubes stacked one on top of the other. Each of the one or more inner segment tubes may have an inlet end and an exit end. The inlet end of the first inner segment tube may be configured to receive a biological sample. The exit end of the first inner segment tubes is connected to the inlet end of second inner segment tube. In a similar manner, all the inner segment tubes are connected forming a vertical stack. The one or more inner segment tubes may be separated into at least two chambers by at least one protein substrate layer.

In another embodiment, a method of and detection of proteolytic activity of a biological sample is disclosed herewith, in accordance with an embodiment of the present disclosure. The method may comprise a step of injecting a biological sample through an outer lid cap into the apparatus. The biological sample may pass through a thin staining layer to a obtain stained biological sample. The stained biological sample may contact at least one of a protein layer positioned inside the one or more inner segment tubes. The stained biological sample may be sustained over at least one of the protein substrate of the inner segment tube until the stained biological sample digests and breaks at least one of the protein layer substrate. The passage of the stained biological sample through the first inner segment to a next inner segment tube may be enabled when at least one of the protein layer is digested by the stained biological sample. The proteolytic activity level of the biological sample may be detected based on number of protein substrate layers digested by the biological sample.

In one embodiment, the level of the matrix metalloproteinases may be detected and assessed on the basis of number of protein layers, digested by the biological sample, of the inner segment tubes.

In still another embodiment, a method of prognosis of oral cancer based on a biological saliva sample from a patient using an apparatus. The biological sample may pass through a thin staining layer to a obtain stained biological sample. The stained biological sample may contact at least one of a protein layer positioned inside the one or more inner segment tubes. The stained biological sample may be sustained over at least one of the protein substrate of the inner segment tube until the stained biological sample digests and breaks at least one of the protein layer substrate. The passage of the stained biological sample through the first inner segment to a next inner segment tube may be enabled when at least one of the protein layer is digested by the stained biological sample. The proteolytic activity level of the biological sample may be detected based on number of protein substrate layers digested by the biological sample.

Other features and advantages of the present invention will be apparent from the following detailed description of the invention which illustrates, by way of example, the principles of the invention.

BRIEF DESCRIPTION OF THE DRAWINGS

The detailed description is described with reference to the accompanying figures. In the Figures, the left-most digit(s) of a reference number identifies the Figure in which the reference number first appears. The same numbers are used throughout the drawing to refer like features and components.

DETAILED DESCRIPTION

Reference throughout the specification to "various embodiments," "one implementation", "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the features, structures or characteristics may be combined in any suitable manner in one or more embodiments.

Various modifications to the embodiment may be readily apparent to those skilled in the art and the generic principles herein may be applied to other embodiments. However, one of ordinary skill in the art may readily recognize that the present disclosure is not intended to be limited to the embodiments illustrated but is to be accorded the widest scope consistent with the principles and features described herein.

Salivary proteome analysis is a potential source of biomarkers for various diseases including cancer. Salivary levels of Gelatinases have long been proposed as a biomarker for prognosis of Oral malignancies and Lung ailments in smokers.

Currently, the detection and risk assessment of oral squamous cell carcinoma (OSCC) is based on clinical oral examination combined with histopathological evaluation of a biopsy sample. These methods are of use only when the tumor/lesion has already appeared. In response to the need for early detection of oral cancer, several diagnostic adjuncts have been developed, including the use of salivary biomarkers. Collecting saliva is a relatively simple procedure and is non-invasive, compared to biopsy or drawing blood.

As used herein, the oral cancer may be any of the following but not limited to Tongue Cancer, Squamous cell carcinoma, Oeosophagus cancer, Verrucous carcinoma, Minor salivary gland carcinomas, Leukoplakia and erythroplakia, and Benign oral cavity tumors.

As used herein, the proteolytic enzyme also known as protease, peptidase or proteinase such as collagenases, gelatinases and proteinases have unique property that catalyzes proteolysis, i.e., such enzymes are characterized for digesting, degrading and breaking down of proteins into smaller polypeptides or single amino acids.

More particularly, the subject matter of present invention illustrates about a device which uses gelatin protein digestion by Gelatinases enzyme as a predictive/prognosis index for risk assessment in a biological sample such as saliva of the subjects and has been standardized to envisage potential threat of malignancy.

The process of metastasis involved series of tumour-host interactions that involve multiple extracellular matrix degrading enzymes, including serine proteinases, cysteine proteinases, and matrix metalloproteinase (MMPs).

Clinical studies revealed that malignant tumour has the ability to hydrolyze the basic components extracellular matrix by the unique action of proteolytic system. A specific group of 24 proteases, collectively called as matrix metalloproteinases (MMPs) are composed of Zinc dependent endopeptidase that degrades proteins of extracellular matrix which is a vital phenomenon associated with cancer. Despite being hundreds of proteinases genes have been identified, MMPs have been heavily implicated in the metastasis.

Alteration in expression and activation of MMPs associated with numerous pathological processes, including the angiogenesis, invasion and metastasis of tumor cells, tissue degradation and inflammatory processes of various organs, shortened the survival in a variety of different cancers.

Based on the efficiency of proteolysis and the composition domains in the family are divided into four main classes: Gelatinase (MMP-2, MMP-9), collagenase (MMP-1, MMP-8, MMP-13), stromelysins (MMP-3, MMP-10, MMP-12) and membrane metalloproteases (MT1-MMP, MT2-MMP, MT3-MMP, MT4-MMP). A typical MMP has a multi-domain structure includes signal peptide, a prodomain, a catalytic domain, a hinge region and hemopexin like domain.

The MMP-2 and MMP-9 are secreted gelatinases, also known as type IV collagenases. These enzymes mainly degrade collagen type IV, important scaffold for the basement membrane proteins and also plays a significant role in regulating and limiting tumour invasion and metastasis. These gelatinases are mainly linked to angiogenesis.

Many clinical and experimental studies have shown that increase in particular MMPs especially MMP-2 and MMP-9 associated with cancer progression. These MMPs are the most common MMPs in head and neck squamous cell carcinoma (HNSCC).

In state of the art, matrix metalloproteinases (MMP) and disintegrins are family of proteolytic enzymes primarily raised in saliva secretions of subjects with high risk of metastatic malignancy especially in lungs and oral cavity provided that other oral pathologies, diabetes, immune system disorders are ruled out. The present disclosure provides a prognosis tool for assessment of proteolytic activity of enzymes matrix metalloproteinases (MMP) such as MMP-9 to MMP-2.

As used herein, the matrix metalloproteinases (MMP) may comprise but not limited to the collagenases such as MMP-1, MMP-8, and MMP-13, gelatinases such as MMP-2, and MMP-9, stromelysins such as MMP-3, MMP-10, and MMP-11, enamelysin such as MMP-20, matrilysin such as MMP-7, and MMP-26, metalloelastase such as MMP-12, membrane type MMPs, and other MMPs such as MMP-19, MMP-21, MMP-23A, MMP-23B, MMP-27, and MMP-28.

As used herein, the term "biological sample" described herein may be any standard test sample comprising matrix metalloproteinases, biopsy sample, biological fluid, body fluid, saliva sample, urine sample, uterine sample, body tissue, swab, a blood sample or any pathological fluid sample, a physiological fluid sample, including, interstitial fluid, sweat, milk, ascites fluid, mucous, and the like.

As described herein, disclosed is specifically developed apparatus acting as a prognosis tool for detection of matrix metalloproteinases (MMP).

Figure 1:
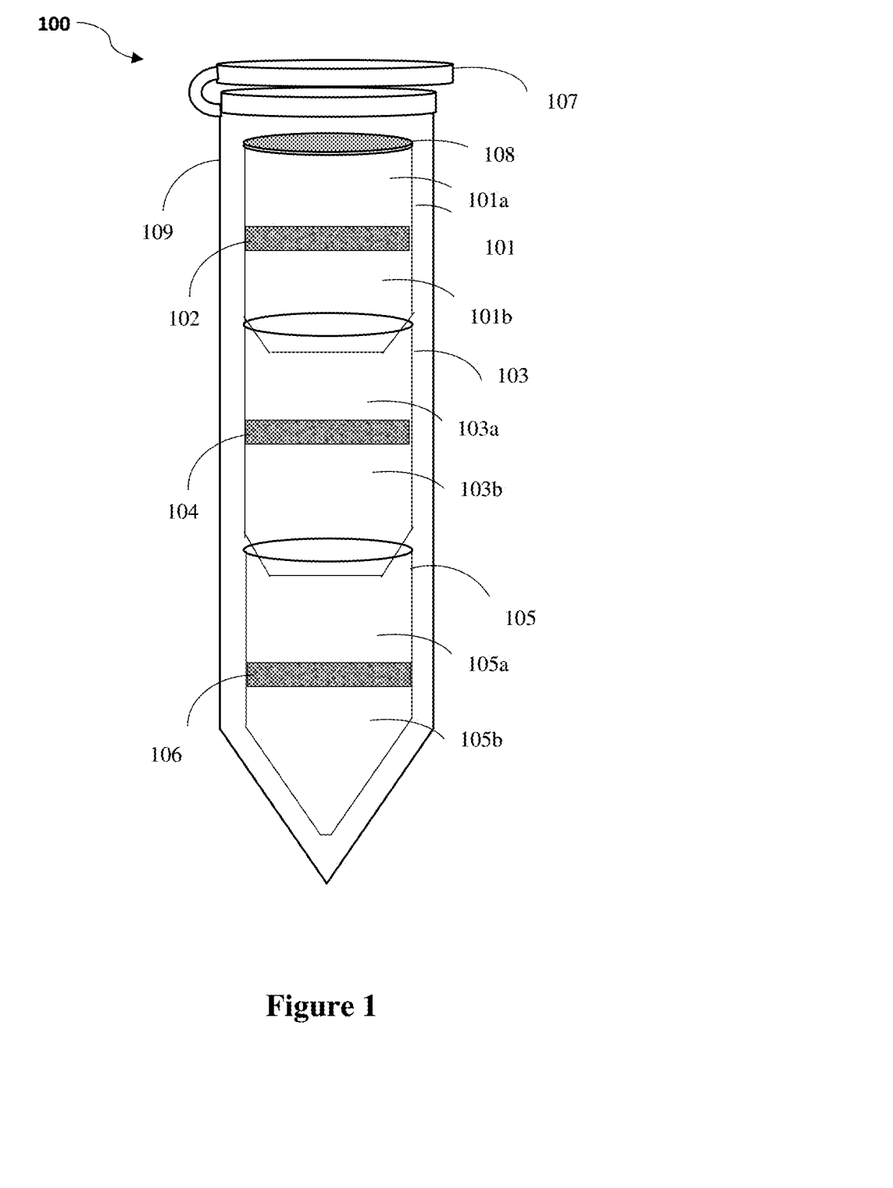
FIG. 1 depicts, an apparatus (100) for detection of proteolytic activity of a biological sample, in accordance with an embodiment of the present disclosure.
Figure 2:
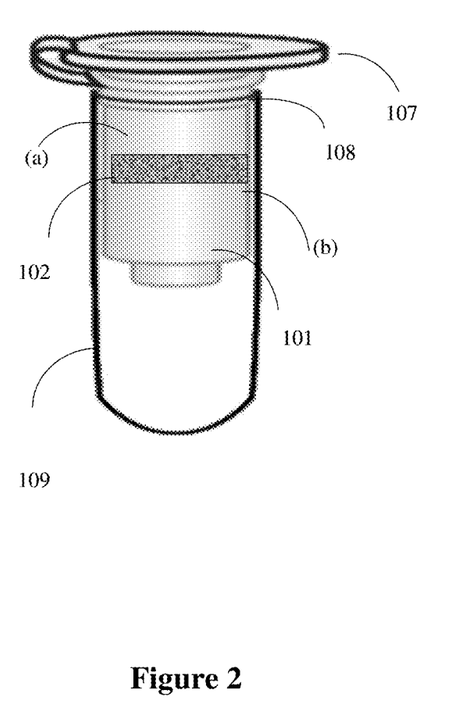
FIG. 2 depicts, an embodiment of the apparatus (100) for detection of proteolytic activity of a biological sample comprising at least one inner segment tube (101), in accordance with an embodiment of the present disclosure.

Referring now to FIG. 1 and FIG. 2, an apparatus (100) for detection of proteolytic activity of an enzyme in a biological sample is illustrated, in accordance with an embodiment of the present disclosure. The apparatus (100) may comprise a tubular outer jacket (109) with a seal cap (107). The apparatus (100) may comprise a one or more inner segment tubes (101, 103, 105) stacked one on top of the other.

In one embodiment, the apparatus (100) may be employed as an 'activity detection kit' detecting the proteolytic activity such as gelatinolytic and collagenolytic activity of matrix metalloproteinases (MMP) proteins and thereby assessing the amount of matrix metalloproteinase in the biological sample.

As used herein, the apparatus (100) may be interchangeably referred to as "kit", "a testing apparatus", "a detection apparatus", "an activity detection apparatus", "an enzyme detection apparatus", "MMP protein enzyme detection apparatus", "a proteolytic activity detection kit', "A Gelatin-based Activity assay kit" etc.

In one embodiment of the present invention, wherein the one or more inner segment tubes (101, 103, 105) are connected to each other at a lower end of each of the one or more tubes (103, 105) and wherein a lower end opening of the first tube (101) is anchored inside an upper end opening of the second tube (103) and a lower end opening of the second tube (103) is anchored inside an upper end opening of the third tube (105). Each of the inner segment tubes (101, 103, 105) comprise a first chamber (101-*a*, 103-*a*, 105-*a*) and a second chamber (101-*b*, 103-*b*, 105-*b*) separated by at least one protein layer (102, 104, 106).

In one embodiment, FIG. 2 illustrates, an embodiment of the apparatus (100) for detection of proteolytic activity of a biological sample may comprise at least one inner segment tube (101), a seal cap (107), the tubular outer jacket (109), a thin auxiliary layer (108) and a protein substrate layer (104). The protein substrate layer (104) is enabled to get digested, consumed or degraded by the biological sample to thereby detect and assess the level of matrix metalloproteinases in the biological sample, in accordance with an embodiment of the present disclosure.

In one embodiment, each of the protein substrate layer (102, 104, 106) may comprise a buffer solution to enhance the storage stability of the apparatus (100). The buffer solution may be any incubation buffer solution. The protein substrate layer (102, 104, 106) may comprise 17 g % of Gelatin solution containing 0.15% Agarose in Incubation Buffer, pH 7.6 (50 mM Tris-HCl, 300 mM NaCl, 5 mM $CaCl_2$), 20 µM $ZnCl_2$).

In another embodiment of the present invention, wherein the individual thickness of protein substrate layer (102, 104, 106) may be at least 1 mm for 50 µl of the biological sample.

Again, referring to FIGS. 1 and 2 of the present disclosure, in one embodiment an upper opening of at least one of the inner segment tube (101, 103, 105) may comprise a thin auxiliary layer (108) comprising a staining agent. The thin auxiliary layer (108) is enabled for staining the biological sample which is injected to the apparatus (100). The thin auxiliary layer (108) is also positioned at the upper opening of at least one of the inner segment tube (101, 103, 105) to observe, understand, assess the passage of the biological sample from the one or more inner segment tubes. In another embodiment, wherein the thin auxiliary layer (108) is enabled for staining and visualize the passage of the biological sample from the one or more inner segment tubes (101, 103, 105), when the biological sample is injected into the apparatus (100).

In one embodiment of the present invention, the staining agent may be a fluorescent dye or a staining dye material. As used herein, examples of staining material may include but not limited to Malachite Green, Safranine, Coomassie Brilliant Blue etc. In yet another embodiment, instead of a separate staining layer, the staining material may directly be introduced into the biological sample before injection of the biological sample into the apparatus (100).

In one embodiment of the present invention, wherein the one or more inner segment tubes (101, 103, 105) are connected to each other in such a way that a lower end opening of the first tube (101) is anchored inside an upper end opening of the second tube (103) and a lower end opening of the second tube (103) is anchored inside an upper end opening of the third tube (105). The one or more inner segment tubes (101, 103, 105) may comprise at least two chambers separated by a protein layer (102, 104, 106).

In one embodiment, the first chamber of at least one of the inner segment tubes (101, 103, 105) is enabled to sustain the stained biological sample over the protein layer substrate (102), until the digestion or breaking of protein layer substrate (102) is carried out by the biological sample.

In yet another embodiment, wherein the second chamber of at least one of the inner segment tube (101, 103, 105) may comprise an air gap, wherein the second chamber is enabled for passage of the stained biological fluid to the next inner segment tube (103) after digestion of the protein layer (102, 104, 106) respectively by the stained biological sample. In one embodiment, each of the inner segment tubes (101, 103, 105) comprise a first chamber (101-a, 103-a, 105-a) and a second chamber (101-b, 103-b, 105-b) separated by at least one protein layer (102, 104, 106).

In still another embodiment, wherein the second chamber (101-b, 103-b, 105-b) of each of the inner segment tubes (101, 103, 105) may be separated from the first chamber (103-a, 105-a) of the next inner segment tubes (103, 105) by an air gap, and wherein the second chamber is enabled for passage of a stained biological fluid to the first inner segment (101, 103) to next inner segment tube (103, 105) after digestion of the protein layer (102, 104, 106) by the stained biological sample.

It must be noted that the rate of digestion or degradation of the protein layer (102, 104, 106) is dependent on the concentration of proteolytic enzyme in the biological sample. If there is low concentration of proteolytic enzyme in the biological sample, then the protein layer (102) will not be degraded. To precisely monitor the degradation of the protein layer (102), a timer may be used to determine the rate at which the protein layer (102) is degraded. In one embodiment, a rate at which at least one of the protein layer (102, 104, 106) is degraded is employed for detection of concentration of proteolytic enzyme in the biological sample.

In one embodiment, each of the protein layer (102, 104, 106) is a protein layer substrate comprising at least one of a protein selected for detection of particular proteolytic activity of the enzyme. Particularly, the protein substrate layer is enabled to get digested by the biological sample and further detection of enzyme matrix metalloproteinases in the biological sample.

In one embodiment, the rate at which the protein layer (102) is degraded can be used to determine the concentration of proteolytic enzyme in the biological sample. Also, the number of protein layers (102, 104, 106) that are degraded by the proteolytic enzyme in the biological sample can also be used to determine the active concentration of proteolytic enzyme in the biological sample.

In another embodiment, wherein at least one of the inner segment tube (101, 103, 105) is enabled to sustain the stained biological sample over at least one of the protein layer substrate (102, 104, 106), until the digestion or breaking of protein layer substrate (102) is carried out by the biological sample. If the whole biological sample is sustained over the first protein substrate layer, then absence of proteolytic enzyme such as MMP-2 and MMP-9 is detected. The detection proteolytic activity level is in the form of expression of MMP-2 and MMP-9 levels in the biological sample for detection of oral cancer. The matrix metalloproteinases level is detected and assessed on the basis of number of protein layers, digested by the biological sample, of the inner segment tubes (101, 103, 105).

In one embodiment, the protein layer substrate (102, 104, 106) inside the inner segment tube (101, 103, 105) may be made of Keratin, Trypsin, Papain, Pepsin, Gelatin and collagen protein. In one embodiment the protein layer substrate (102, 104, 106) may be comprising a specific protein selected from at least one of Gelatin and collagen used for detection of particular proteolytic activity of an enzyme. In one the protein layer substrate (102, 104, 106) inside the inner segment tube (101, 103, 105) may be a predetermined combination of one or more proteins substrates.

Optionally, the tubular outer jacket (109) may be a form of measuring apparatus with a cylindrical or a cubical shape, with a measurement marking ruler enabled for assessing the degradation of protein layer and further enabled for assessing a reachability of the downward flow the biological fluid in the apparatus (100).

Figure 4:
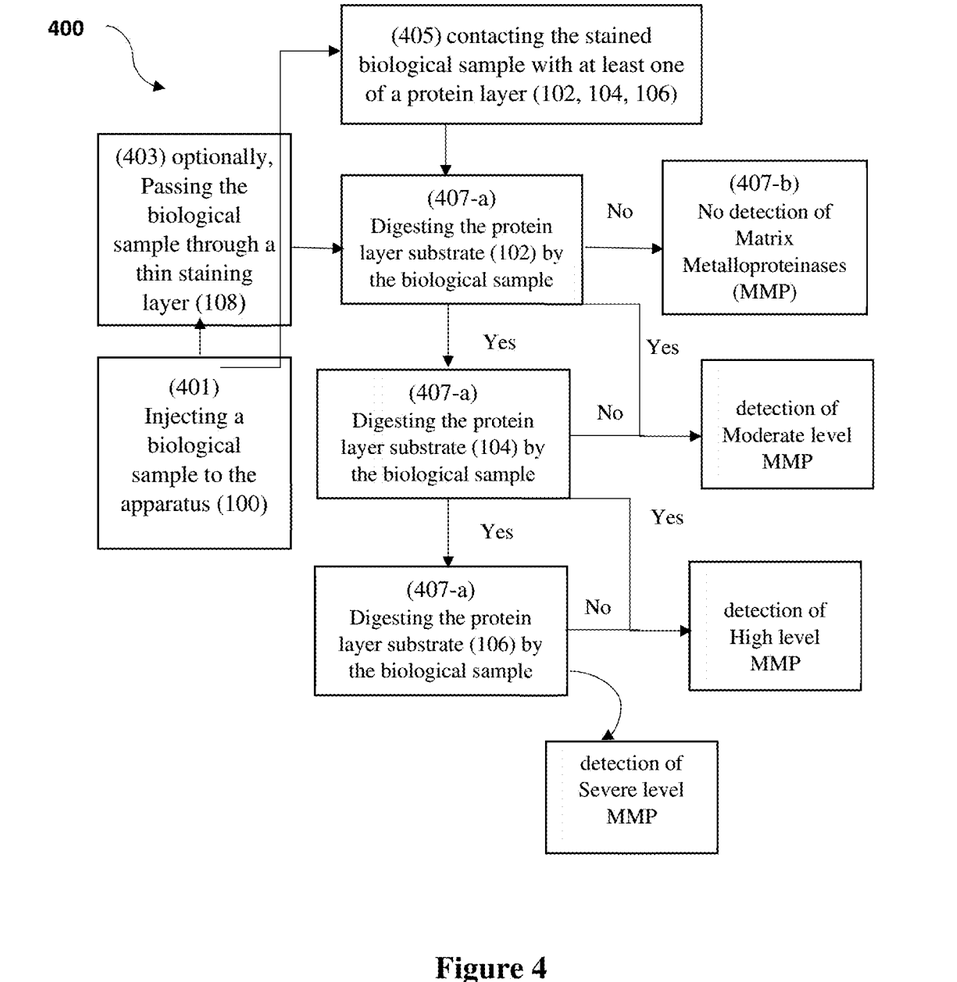
FIG. 4 depicts, a method (400) of assessment and detection of proteolytic activity of a biological sample, in accordance with an embodiment of the present disclosure.

Referring to FIG. 4, a method (400) of assessment and detection of proteolytic activity of a biological sample is illustrated in accordance with an embodiment of the present disclosure.

In one embodiment, a method (400) of assessment and detection of proteolytic activity of a biological sample using apparatus (100) is disclosed herewith. At step (401) injecting, a biological sample through an outer lid cap (107) to a obtain stained biological sample into the apparatus (100) is performed.

In another embodiment, the biological sample may pass through a thin staining layer (108) to a obtain stained biological sample. The stained biological sample may further contact at least one of a protein layer (102, 104, 106) positioned inside the one or more inner segment tubes (101, 103, 105). In one scenario, the stained biological sample may be sustained over at least one of the protein substrate (102, 104, 106) of the inner segment tube (101, 103, 105), until the stained biological sample digests and breaks at least one of the protein layer substrate (102, 104). In yet another scenario, passage of the stained biological sample through the first inner segment (101, 103) to a next inner segment tube (103, 105) may be enabled, when at least one of the protein layer (102, 104, 106) is digested by the stained biological sample. Thereby, a proteolytic activity level of the biological sample is detected based on number of protein substrate layers digested by the biological sample.

Referring to FIGS. 1 and 4, At block (403), the biological sample is passed through a thin staining layer (108) for staining the biological sample and to obtain stained biological sample. The stained biological sample is then approached towards a first compartment of the first inner segment tube (101).

At block (405), contacting the stained biological sample with at least one of a protein layer (102, 104, 106) positioned inside the one or more inner segment tubes (101, 103, 105) takes place. In one embodiment, the protein substrate layer (102, 104, 106) may be colored with different color stains such as, yellow, orange and red respectively. The color staining of the protein substrate layer may be enabled to represent risk assessment and level of detection of proteolytic activity in the biological samples.

At block (407-a), the digestion or degradation of at least one of the protein layer (102, 104, 106) may start when a definite amount of Matrix Metalloproteinases (MMP) is present in the stained biological sample. In one embodiment, at step (407-a) the stained biological sample comprising a matrix metalloprotein enzyme may digest the whole protein substrate layer (102) and may further pass towards the second inner segment (103) tube from the second chamber of the first tube (101).

In another scenario, alternatively at block (407-b) the stained biological sample without any traces of matrix metalloprotein enzyme may not digest the protein layer substrate and may stay on top of the protein substrate layer (102) keeping the protein substrate layer intact, when no Matrix Metalloproteinases (MMP) is present in the stained biological sample. Alternatively, at step (407-b) the stained biological sample is sustained over at least one of the protein layer (102, 104, 106) when no Matrix Metalloproteinases (MMP) is present in the stained biological sample.

In yet another embodiment, wherein at block (407-a) the stained biological sample comprising a matrix metalloprotein enzyme may digest the protein layer substrate (104) completely/partially and may further pass towards the third inner segment (105) tube from the second chamber of the second tube (103). In one embodiment, at step (407-b) the stained biological sample comprising a matrix metalloprotein enzyme may digest the whole protein layer substrate (106) and may further pass towards the next inner segment tube from the second chamber of the third tube (105).

In still another embodiment, at block (409) a proteolytic activity level of the biological sample and thereby level of Matrix Metalloproteinases (MMP) in the biological sample may be detected by the apparatus (100).

In one embodiment, an assessment of presence of matrix metalloproteinases in the biological sample may be performed based on the number of protein layers digested by the biological sample. In another embodiment, the assessment of presence of matrix metalloproteinases in the biological sample is performed based on the reachability of the biological fluid to the second chamber of at least one inner segment tube.

In one embodiment, the digestion of first protein substrate layer may detect presence at least 30 ng/ml MMP-9 or MMP-2 enzyme in the biological sample and thereby detecting the moderate lever of Matrix Metalloproteinases (MMP).

In another embodiment, the method (400) is a method of prognosis of oral cancer based on a biological saliva sample from a patient using an apparatus (100).

EXAMPLES

Example 1

In one implementation, detection of MMP-2 and MMP-9 (Gelatinase A and B respectively) in the saliva sample by proteolytic activity detection kit (100) is performed. The proteolytic activity detection kit (100) is based on the biochemical reactions and further checks for the biomarker which is released in moderate to high quantities causing damage to the extracellular matrix of the cell and thereby indicating whether the carcinogenic cell metastasis has taken place being reflected in the biological sample.

An apparatus (100) comprising three even layers (102, 104, 106) of 17 g % of Gelatin solution containing 0.15 Agarose in incubation buffer with pH 7.6, (50 mM Tris-HCl, 300 mM NaCl, 5 mM $CaCl_2$, 20 µM ZnCl2) and positioned in the three inner segment tubes (101, 103, 105) anchored with each other inside the tubular outer jacket (109) is developed for the detection of detection of MMP-2 and MMP-9 (Gelatinase A and B respectively) in the saliva sample. The individual thickness of protein layer (102, 104, 106) may be at least 1 mm for 50 ul of the biological sample. The kit (100) comprises a thin staining layer (108) on top of the first inner segment tube for initial staining of the saliva sample.

Further, a 10 µl of fresh early morning pre-centrifuged saliva sample was injected in the proteolytic activity detection kit (100). The saliva sample was kept idle for 10 minutes in the first inner segment tube. The assessment of the gelatinolytic activity of the saliva sample was performed.

Observations

It was observed that, after completion of 10 minutes the samples consisting of proteolytic enzyme break and digest the gelatin layer substrate of the first inner segment tube (101) and flows downwards to reach the second inner segment tube (103) confirming the positive detection of MMP-2 and MMP-9 enzyme in the saliva sample. In another scenario, the saliva sample of healthy individual with no traces or minimal amount of MMP-2 and MMP-9 sustained over the stayed on top of the gelatin substrate layer (102) in the first inner segment tube (102) even after an hour.

In one embodiment, the level of matrix metalloproteinase in the biological sample is assessed based on the reachability of the biological fluid/sample as not present, moderate level, high level and severe level.

Figure 3:
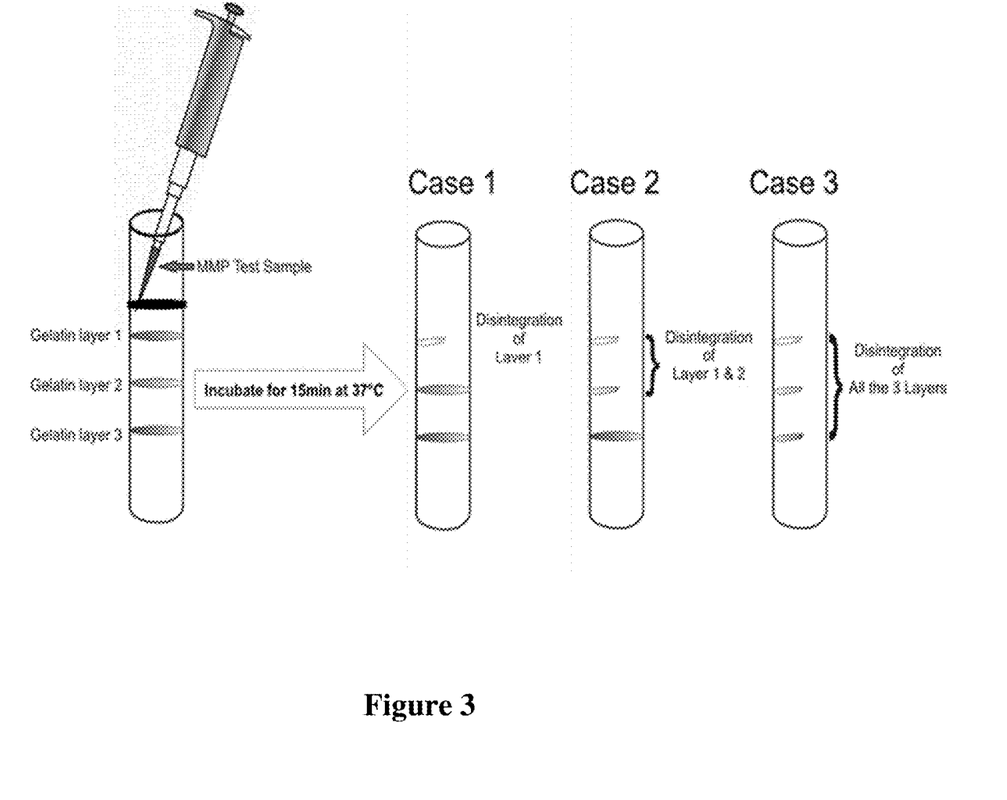
FIG. 3 depicts, a scheme for assessment of proteolytic activity of proteolytic enzymes in the biological sample, in accordance with an embodiment of the present disclosure.

In one embodiment, FIG. 3 illustrates, a scheme for assessment of proteolytic activity of proteolytic enzymes in the biological sample, in accordance with an embodiment of the present disclosure.

Referring to FIG. 3 and FIG. 4, as assessment and detection of Matrix Metalloproteinases (MMP) level in the biological sample based on the reachability of the biological fluid in the apparatus/kit (100) may be described by the table 1.

TABLE 1

| Reachability of the biological fluid | Detection of Matrix Metalloproteinases (MMP) level |
|---|---|
| No digestion/consumption of any of protein layer | No |
| Presence of the biological fluid in the second chamber of first inner segment tube | Moderate level |
| Presence of the biological fluid in the second chamber of second inner segment tube | High level |
| Presence of the biological fluid in the second chamber of third inner segment tube | Severe level |

Example 2

In another example, the saliva sample as prepared in Example 1 is injected to the MMP enzyme detection kit (100) comprising Three even protein substrate layers (102, 104, 106) comprising of 17 g % of Gelatin solution containing 0.15% Agarose in Incubation Buffer, pH 7.6 (50 mM Tris-HCl, 300 mM NaCl, 5 mM $CaCl_2$, 20 µM $ZnCl_2$) with individual thickness of 1 mm Human Recombinant MMP-2 (AnaSpec, Inc., USA Cat #72005) and MMP-9 (AnaSpec, Inc., USA Cat #55576) were used to standardize the Test.

Results

Approximately ≥0.2 µg/ml of activated MMP-2 and ≥120 ng/ml of MMP-9 were individually found to completely digest the three gelatin layers within 15 min of incubation at 37° C. Whereas a minimum of 30 ng/ml of activated MMP-2 and 21 ng/ml of MMP-9 were capable of showing digestion of single gelatin layer in 15 min time frame of incubation at 37° C.

Referring to FIG. 3-4, and Example 1-2, The gelatinase level in the saliva sample is detected and assessed as below:

TABLE 2

| Permissible Salivary Gelatinase Level | Digestion of the first protein substrate layer (102) | 21- 40 ng/ml | (Negligible risk of Malignancy) |
| Moderately Elevated Salivary Gelatinase Level | Digestion of the second protein substrate layer (104) | 40-160 ng/ml | (Moderate risk of Malignancy) |

TABLE 2-continued

| Highly Elevated Salivary Gelatinase Level | Digestion of the third protein substrate layer (106) | ≥170 ng/ml | (High risk of Malignancy) |

Example 3

Material and Method
Sample Collection:

Early morning whole saliva sample was collected in separate tube before administrative use at least 1 hour before eating, drinking and abiding to proper oral hygiene procedure. Patients were asked to donate their saliva after rinsing their mouth well for 1 min and thereafter spit was collected into a wide sterile tube up to 5 ml. Following the collection, the saliva was immediately centrifuged at 4000 g for 15 min at 4° C. to remove squamous cell and cell debris. The resulting supernatant was then transferred to another tube and stored for further biochemical analysis at −20° C.

Protein Estimation:

Total protein content in each sample is estimated by the Lowry's method of Protein estimation and the protein concentration was determined against standard Bovine serum albumin (BSA).

The saliva sample of the Example 3 is analyzed for detection of presence of Matrix metalloproteinases using existing complicated and expensive methods such as Enzyme-Linked Immunosorbant assay (ELISA), and Gelatin Zymography. The results obtained by performing the method (400) for detection of a proteolytic activity level of a biological sample using an apparatus (100) are compared with the Enzyme-Linked Immunosorbant assay (ELISA), and Gelatin Zymography methodologies.

MMP Activity Assay:

The spectrophotometric assay of MMPs activity was done as per manufacturer's instruction using the Sensolyte Generic MMP Assay kit (AnaSpec, Inc., USA Cat #AS-72095). Briefly the kit relies on MMP dependent cleavage of a modified substrate, thiopeptolide, releasing a sulfhydryl group. This sulfhydryl group reacts with Ellman's reagent (5, 5'-dithiobis (2-nitrobenzoic acid). The final product of this reaction, 2-nitro-5-thiobenzoic acid (TNB), can be detected at 412 nm and the concentration of free sulphydryl (SH) groups generated as a result of MMP action are quantified against standard reduced glutathione (GSH).

Total MMP-9 Content Estimation by Enzyme-Linked Immunosorbant Assay (ELISA):

Total (pro and active) MMP-9 quantification in the samples was done by ELISA using commercial available Human MMP9 (Matrix Metalloproteinase 9) ELISA Kit (MyBioSource, Inc., USA, Catalog No: MBS2512591) as per manufacturer's instructions briefly described below:

This kit contained pre-coated antibody specific to Human MMP-9. Standards or samples combined with specific antibody were added in the 96-well microtitre plate. Then biotinylated detection antibody specific for human MMP-9 and Avidin-Horseradish Peroxidase (HRP) conjugate are added and incubated for specified time period at 37° C. Followed by a washing step the chromogenic TMB-$H_2O_2$ substrate solution was added to each well. Only those contain Human MMP-9, biotinylated antibody and Avidin-HRP conjugate will appear blue in color. This reaction is stopped by the addition of acidic stop solution and optical density is measured at 450 nm which is proportional to the concentration of Human MMP-9. Concentration of Human MMP-9 in the samples comparing to the OD of the samples to the standard curve can be calculated.

Gelatin Zymography:

Gelatin Zymography was performed as described by Tajhya et. al with little modifications (containing 3 mg/ml gelatin). The MMP samples were mixed with the sample loading buffer dye without reducing agent and electrophoresis was performed in 10% SDS polyacrylamide gel at 4° C. for approximately 2 hrs. After gel electrophoresis the gel was washed four times for 30 min each using washing buffer [containing 25 ml 1M Tris (pH 7.6), 5 ml 1M $CaCl_2$, 500 µl 0.5M$ZnCl_2$, 12.5 ml Triton-X 100 dd$H_2O$ to 1 L.] followed by 2× rinse with ddH2O. Then finally washing the gel with incubation buffer for 30 min then incubating at 37° C. overnight in incubation buffer/developing buffer [containing 25 ml 1M Tris (pH 7.6), 55 ml 1M NaCl, 20 min Glycine, 1 µM Zinc chloride ddH2O to 1 L.] causes activation of MMPs in the sample. The incubation buffer is discarded the following day and 2× rinse with dd$H_2O$ is done to add staining solution (containing 40% methanol, 10% acetic acid 0.1% CBB-R250) for 1 hour further to de-stain the gel with de-staining solution (containing 40% methanol, 10% acetic acid) to visualize the unstained halos created by active MMPs in the gel. The image analysis of the gel was performed using gel BioRad gel documentation system. Standard Human MMP-2 (AnaSpec, Inc., USA Cat #72005) and—9 (AnaSpec, Inc., USA Cat #55576) served as to estimate approximate quantities of MMP-2 and MMP-9 in the tested samples.

Gelatin-Based Activity Assay Using the Apparatus (100):

17 g % of Gelatin solution containing 0.15% Agarose in buffer [containing 50 mM Tris-HCl (pH 7.6), 300 min NaCl 5 min $CaCl_2$, 20 min $ZnCl_2$.] was boiled to get a clear solution which was maintained at 55° C. for further use. Three even layers of Gelatin in Incubation Buffer, pH 7.6 (50 mM Tris-HCl, 300 min NaCl, 5 min $CaCl_2$, 20 µM $ZnCl_2$) with individual thickness of 1 mm were prepared in the as shown in the FIGS. 1 and 2 and in the Apparatus (100). Human Recombinant MMP-2 (AnaSpec, Inc., USA Cat #72005) and MMP-9 (AnaSpec, Inc., USA Cat #55576) were used to standardize the Test. An amount 50 µl of the saliva sample (biological sample) was used in each tube for the test and incubated at 37° C. for 15 min to observe the Gelatin degradation and thereby to determine the proteolytic activity of the biological sample.

Statistical Analysis:

All the assessments described were performed in at least 3 independent replicates unless otherwise specified. Standard deviations calculated using MS excel were shown as error bars in the respective graphical representations.

Results:

Total MMP-9 Content Estimation by ELISA:

Total MMP-9 concentration of the samples was assessed using the Human MMP9 (Matrix Metalloproteinase 9) ELISA Kit (MyBioSource, Inc., USA, Cat #MBS2512591) wherein even the concentration of standard MMP-9 (AnaSpec, Inc., USA Cat #55576) was tested along with the standard provided in the kit. Following was the standard curve from which based on the equation of the curve the MMP-9 concentration of the samples were determined.

TABLE 3

| Sample | Concentration of Human MMP-9 in pg/ml |
|---|---|
| S1 | 1234.341086 |
| S5 | 2403.184073 |
| S6 | 1080.350842 |
| S7 | 2103.374801 |
| S8 | 425.0815174 |
| MMP-9 (AnaSpec, Inc., USA Cat#55576) | 325.6353028 |

It is observed that, the conventional MMP-9 quantification (ELISA) method was used to determine the exact concentration of the MMP-9 in the patient saliva samples and accordingly the amount of MMP-9 put to assess the scale risk of oral cancer using the test kit comprising apparatus (100). Considering to the inherent drawback of the conventional ELISA method, which may also determine pro-MMP-9 rather than active MMP-9 and also fails to predict MMP inhibitor levels, the colorimetric MMP activity determination method (Sensolyte) was utilized to correlate MMP-9 concentration determined by ELISA with its corresponding activity in terms of reduced glutathione.

Figure 5:
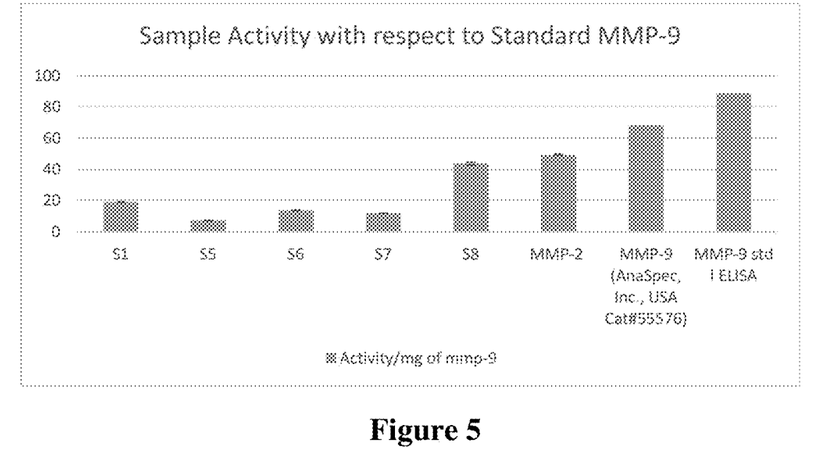
FIG. 5 depicts extrapolation of the activity of each sample as an estimate of free sulphydryl group equivalents per mg of MMP-9 (Activity/mg of MMP-9) in accordance with an embodiment of the present invention.

MMP Activity Assay:

The spectrophotometric assay of MMP activity performed using the Sensolyte Generic MMP Assay kit (AnaSpec, Inc., USA Cat #AS-72095) was utilized to estimate the reduced glutathione (GSH) equivalents by estimating free sulphydryl groups produced from MMP digested thiopeptolide substrate provided with the kit, as calculated from the GSH standard curve which is illustrated in FIG. 5.

Referring to FIG. 5, the reduced glutathione (GSH) equivalents of free sulphydryl groups thus estimated are extrapolated for per mg of MMP-9 amount as estimated by the ELISA kit detailed above. Thereby the activity of each sample as an estimate of free sulphydryl group equivalents per mg of MMP-9 (Activity/mg of MMP-9) is calculated as given in the FIG. 5.

Figure 6:
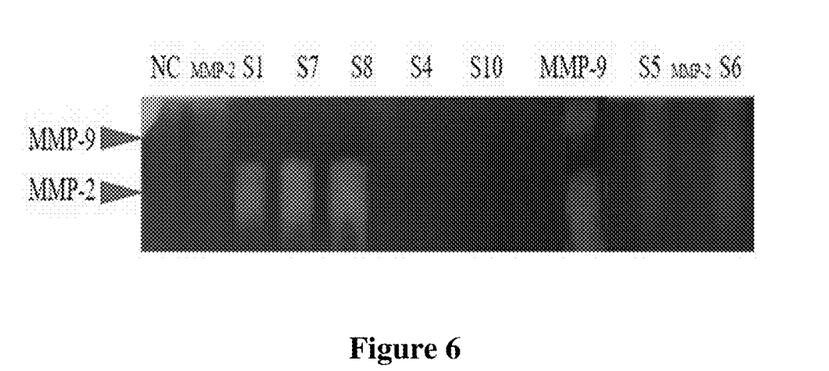
FIG. 6 depicts a gelatin zymography with saliva samples and MMP-2 and MMP-9 standards to get an approximate estimate of the active MMP-2 and MMP-9 content of the patient saliva samples in accordance with an embodiment of the present invention.

Gelatin Zymography:

The zymography was performed with saliva samples and MMP-2 and MMP-9 standards to get an approximate estimate of the MMP-2 and MMP-9 content of the patient saliva samples. The results obtained are represented in FIG. 6.

10 ng of MMP standards were in each well and correspondingly similar quantity of each patient sample was also loaded. The best gelatinase activity was demonstrated by samples S1, S7 and S8 but perhaps due to uneven quantities of MMPs S5 and S6 appeared very weakly active in the zymography. This result also goes along with the activity profile as estimated by the spectrophometric assay kit as well as Gelatin-based assay kit described below. As the samples S4 and S10 failed to demonstrate any significant activity in zymography and Gelatin based assay they were not tested in spectrometric and ELISA protocols.

Gelatin-Based Activity Assay Using the Apparatus (100):

Approximately ≥0.2 µg/ml of activated MMP-2 and ≥120 ng/ml of MMP-9 were individually found to completely digest the three gelatin layers within 15 min of incubation at 37° C. Whereas a minimum of 30 ng/ml of activated MMP-2 and 21 ng/ml of MMP-9 were capable of showing digestion of single Gelatin layer in 15 min time frame of incubation at 37° C. The amount of MMP was confirmed in accordance with the estimates determined from standard ELISA kit.

Therefore, based on above comparative observation, the present Apparatus (100) and method (400) of detection of proteolytic i.e., gelatinolytic activity of the said biological sample as saliva sample has shown to be developed as prognostic/diagnostic tool for MMP-2 and MMP-9 activity detection taken together rather than individually in saliva sample. This test kit (100) may predict the likeliness of malignancy if MMP detection is done in body fluids within close proximity to precancerous and/or premalignant legions.

In one embodiment, the said apparatus (100) may provide and enable a scale for risk assessment of plausible malignancy chance despite absence of any visual clinical feature/lesion via detection of gelatinolytic activity of MMP in saliva as under and detailed in the scheme of the assay and in the table below.

Permissible Salivary Gelatinase Level (Negligible Chance of Malignancy) 21-40 ng/ml Moderately Elevated Salivary Gelatinase Level (Moderate Chance of Malignancy) 40-160 ng/ml Highly Elevated Salivary Gelatinase Level (High Chance of Malignancy)≥170 ng/ml

TABLE 4

| Biological saliva Samples | Test 1 | Test 2 | Test 3 |
| --- | --- | --- | --- |
| S1 | + + + | + + + | + + |
| S5 | + + | + + | + + |
| S6 | + + + | + + | + + |
| S7 | + + + | + + + | + + + |
| S8 | + + + | + + + | + + + |
| S4 | −ve | −ve | −ve |
| S10 | −ve | −ve | −ve |
| Total time recording 15 min | | | |

+, ++, +++ - Indicates 1, 2 and 3 layer digestion of Gelatin corresponding to the low, moderate and high risk levels of active MMPs in sample respectively for prediction of susceptibility for oral cancer
−ve - indicates No Gelatin layer digestion indicative of negligible active MMP levels in sample and negligible risk of oral cancer.

Through the present Apparatus (100) intends to propose a scale for risk assessment of plausible malignancy chance despite absence of any visual clinical feature/lesion via detection of gelatinolytic activity of MMP-2 and MMP-9 in saliva.

In one embodiment, the said apparatus (100) for detection of proteolytic activity of the biological body fluid sample may act as semi-quantitative kit that appears to give results at par to the most sophisticated and accurate methods of MMP quantifications commercially available in the market. Also, the Apparatus (100) partially alleviates the drawbacks of the presently employed methods and makes a reliable estimate of MMP activity with maximum ease. Therefore, the said proteolytic activity detection kit (100) advantageous over the other expensive detection methods being a non-invasive and inexpensive way for early detection of oral cancer.

In one embodiment of the present invention, referring to Example 4 following observations were made:

The detection of gelatinolytic activity of the MMP enzyme using Apparatus (100) is observed to be economic and rapid prognosis kit to determine disease consequences associated with it which conventionally could be determined only by some expensive and technically demanding methods like the colorimetric assay.

Moreover, encouraging fact was however that when the saliva samples as well as standard MMP-9 were subjected to test in using the apparatus (100) for detection of proteolytic activity of an enzyme and for assessing the level of matrix metalloproteinases in a biological sample, the results indicated that the sensitivity of the present Apparatus (100) was comparable to conventional expensive colorimetric assay method. T Thus, as pert the disclosure of present invention the Apparatus (100) which serves as a gelatinolytic activity detection kit provides a preliminary estimate of active MMP levels may act as a predictor of disease progression.

Also, the method (400) only requires basic sample pre-processing, which is cost effective, easy to perform and requires a very minimum amount of sample. Therefore, a gelatinolytic activity detection kit (100) is cheaper, sensitive and a better substitute to conventional protease activity test methods.

In accordance with embodiments of the present disclosure, the apparatus (100) for detection of proteolytic activity of an enzyme and for assessing the level of matrix metalloproteinases in a biological sample as described above may have following advantages including but not limited to:

The enzyme detection apparatus (100) is a portable and inexpensive system.

The testing apparatus is enabled for assessing the likeliness of malignancy if MMP detection is perceived in the provided biological sample.

The testing apparatus is enabled for assessing the level of proteolytic enzymes to provide visual results in lesser amount of time.

The foregoing applications of the apparatus/kit developed and disclosed herewith may include but not limited to detection of proteolytic activity of MMP enzymes and other proteolytic enzymes such as collagenases, gelatinases etc.

The invention claimed is:

1. An apparatus (100) for the detection of a proteolytic activity level of a biological sample, the apparatus (100) consisting of:

two or more inner segment tubes (101, 103, 105) stacked one on top of the other; a cross-sectional thin auxiliary layer (108), consisting of a staining agent, at an upper opening of at least one of the inner segment tubes (101, 103, 105); a tubular outer jacket (109) with a seal cap (107), wherein the inner segment tubes (101, 103, 105) are stacked in the tubular outer jacket (109); and a cross-sectional protein substrate layer (102, 104, 106) having an individual thickness of at least 1 mm within each of the inner segment tubes (101, 103, 105), wherein the apparatus (100) detects the proteolytic activity level of the biological sample based on the number of protein substrate layers (102, 104, 106) digested by the biological sample, as the biological sample passes from a first inner segment tube (101, 103) to a next inner segment tube (103, 105).

2. The apparatus (100) of claim 1, wherein two or more inner segment tubes (101, 103, 105) are stacked one above the other, and wherein a lower end opening of the first tube (101) is anchored inside an upper end opening of the second tube (103) and a lower end opening of the second tube (103) is anchored inside an upper end opening of the third tube (105).

3. The apparatus (100) of claim 1, wherein each of the inner segment tubes (101, 103, 105) consists of a first chamber (101-a, 103-a, 105-a) and a second chamber (101-b, 103-b, 105-b) separated by at least one protein substrate layer (102, 104, 106).

4. The apparatus (100) of claim 3, wherein at least one of the inner segment tubes (101, 103, 105) sustains the stained biological sample over at least one of the protein substrate layers (102, 104, 106) until the digestion or breaking of the protein substrate layer (102) is carried out by the biological sample.

5. The apparatus (100) of claim 4, wherein the second chamber (101-b, 103-b, 105-b) of each of the inner segment tubes (101, 103, 105) is separated from the first chamber (103-*a*, 105-*a*) of the next inner segment tube (103, 105) by an air gap, and wherein the stained biological material passes downward from the second chamber in the first inner segment tube (101, 103) to the first chamber of the next inner segment tube (103, 105) after digestion of the protein layer (102, 104, 106).

6. The apparatus (100) of claim 1, wherein a rate at which at least one of the protein substrate layers (102, 104, 106) is degraded depends on the concentration of a proteolytic enzyme in the biological sample.

7. The apparatus (100) of claim 1, wherein the staining agent is a fluorescent dye material consisting of at least one of malachite green dye and safranine.

8. The apparatus (100) of claim 6, wherein the proteolytic enzyme consists of one or more metalloproteinases selected from MMP-2 and MMP-9.

9. The apparatus (100) of claim 4, wherein at least one of the protein substrate layers (102, 104, 106) consists of gelatin and/or collagen protein for detection of a particular proteolytic activity of an enzyme in the biological sample.

10. The apparatus (100) of claim 1, wherein a protein in the protein substrate layer is digested by matrix metalloproteinases in the biological sample.

11. The apparatus (100) of claim 1, wherein the thin auxiliary layer (108) stains the biological sample when the biological sample is injected into the apparatus (100).

12. The apparatus (100) of claim 1, wherein the proteolytic activity level is an expression of MMP-2 and MMP-9 level in the biological sample for detection of an oral cancer.

13. A method (400) for detection of a proteolytic activity level of a biological sample using an apparatus (100), the method comprising steps of:
   injecting (401) a biological sample through a seal cap (107) into the apparatus (100); wherein the biological sample passes through a thin auxiliary layer (108) to a obtain a stained biological sample, wherein the stained biological sample contacts at least one protein substrate layer (102, 104, 106) positioned inside the one or more inner segment tubes (101, 103, 105), wherein the stained biological sample is sustained over at least one of the protein substrate layers (102, 104, 106) of the inner segment tubes (101, 103, 105), until the stained biological sample digests and breaks at least one of the protein substrate layers (102, 104), and wherein the stained biological sample passes through the first inner segment tube (101, 103) to a next inner segment tube (103, 105), when at least one of the protein substrate layers (102, 104, 106) is digested by the stained biological sample.

14. A method (400) of prognosis of oral cancer based on a biological saliva sample from a patient using an apparatus (100), characterized in that the method (400) comprises: injecting (401) a biological sample through a seal cap (107) into the apparatus (100); wherein the biological sample passes through a thin auxiliary layer (108) to obtain a stained biological sample, wherein the stained biological sample contacts at least one protein substrate layer (102, 104, 106) positioned inside the one or more inner segment tubes (101, 103, 105), wherein the stained biological sample is sustained over at least one of the protein substrate layers (102, 104, 106) of the inner segment tubes (101, 103, 105), until the stained biological sample digests and breaks at least one of the protein substrate layers (102, 104), and wherein the stained biological sample passes through the first inner segment (101, 103) to a next inner segment tube (103, 105), when at least one of the protein substrate layers (102, 104, 106) is digested by the stained biological sample.

* * * * *